United States Patent [19]

Haslanger

[11] 4,325,891

[45] Apr. 20, 1982

[54] METHOD FOR PREPARING KETOPINIC ACID HALIDES AND THE FREE ACID THEREOF

[75] Inventor: Martin F. Haslanger, Lambertville, N.J.

[73] Assignee: E. R. Squibb & Sons, Inc., Princeton, N.J.

[21] Appl. No.: 216,344

[22] Filed: Dec. 15, 1980

[51] Int. Cl.$^3$ ............ C07C 51/58; C07C 51/04
[52] U.S. Cl. ............................ 260/544 L; 562/502
[58] Field of Search ............... 260/544 L; 562/500, 562/502

[56] References Cited

PUBLICATIONS

Bartlett, Paul D. et al. *J. Am. Chem. Society*, (1939) vol. 61, pp. 3184–3192 at p. 3189.

*Primary Examiner*—Natalie Trousof
*Assistant Examiner*—L. Hendriksen
*Attorney, Agent, or Firm*—Lawrence S. Levinson; Burton Rodney

[57] ABSTRACT

A method is provided for converting 10-halosulfinylidenecamphor to ketopinic acid halide or ketopinic acid.

10 Claims, No Drawings

METHOD FOR PREPARING KETOPINIC ACID HALIDES AND THE FREE ACID THEREOF

The present invention relates to a method for converting 10-halosulfinylidenecamphor to ketopinic acid halide or to the free acid thereof.

Chiral ketopinic acid halides are useful for resolving optical isomers of alcohols as described in Woodward et al., J. Am. Chem. Soc., 95, 6853 (1973).

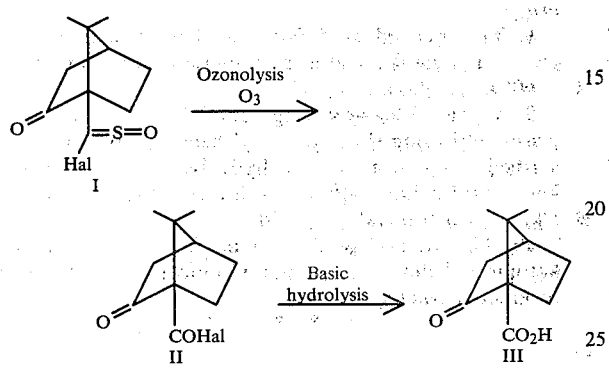

The method of the present invention is illustrated by the above reaction sequences and includes the steps of subjecting a basic solution of 1-10-halo-10-sulfinylidenecamphor I to ozonolysis at reduced temperatures to form the 1-ketopinoylhalide II.

The so-formed 1-ketopinoylhalide is converted to the free acid III by basic hydrolysis, for example, by reaction with a strong base.

In carrying out the method of the invention, a starting material such as 1-10-chloro-10-sulfinylidenecamphor or 1-10-bromo-10-sulfinylidenecamphor the former being preferred, (the preparation of which is described in J. Strating, Rec. Trav. Chim. Pays-Bas, 83, 94 (1964)) is subjected to ozonolysis, for example, for reacting same with ozone, in the presence of an organic base such as pyridine, methylated pyridines, dimethylated pyridines, triethylamine and the like and an inert chlorinated hydrocarbon solvent such as dichloromethane, dichloroethane or other inert solvent which will not freeze during the reaction. The reaction is carried out at a temperature of within the range of from about −40° C. to about −100° C., and preferably from about −60° C. to about −90° C. employing a molar ratio of starting camphor compound to ozone of from about 0.2:1 to about 1:1 and preferably from about 0.9:1 to about 1:1. The organic bases will be employed in a molar ratio to the starting camphor compound of within the range of from about 3:1 to about 1:1, with the chlorinated hydrocarbon solvent being employed in sufficient amount to insure dissolution of the starting camphor compound.

The 1-ketopinic free acid is simply prepared from the 1-ketopinoyl halide by subjecting same to basic hydrolysis by treatment with an alkali metal hydroxide, such as potassium hydroxide or sodium hydroxide or an alkaline earth metal hydroxide, such as magnesium hydroxide or calcium hydroxide, in the presence of a water-immiscible solvent, such as tetrahydrofuran, dioxane and the like. The base will be employed in a molar ratio to the 1-ketopinoyl halide in an amount of from about 1:1 to about 10:1 and preferably from about 2:1 to about 6:1.

Although the above method is described employing the starting material in the form of its 1-isomer, the starting 10-halo-10-sulfinylidenecamphor compound may be employed as a racemic mixture or as each optical antipode.

Where the starting material is employed in the form of a racemic mixture, the final product whether it be the halide or free acid may be resolved into its optical antipodes employing conventional procedures, as desired.

The 10-halo-10-sulfinylidenecamphor starting material is prepared as described by J. Strating, Rec. Trav. Chim. Pays-Bas, 83, 94 (1964) as follows: A mixture of p-toluenesulfonyl halide and organic base, such as pyridine, are heated on a steam bath and to the heated mixture is added 10-camphorsulfonyl halide. The reaction mixture is heated and then cooled and poured into ether. A solid separates which is digested with ether. The combined ether solutions are concentrated to yield the 10-halo-10-sulfinylidenecamphor.

The following Examples illustrate preferred embodiments of the present invention. All temperatures are expressed in °C.

EXAMPLE 1

1-Ketopinic acid chloride

A solution of 47.8 g (0.206 mole) of 1-10-chloro-10-sulfinylidenecamphor (prepared as described in J. Strating, Rec. Trav. Chim. Pays-Bas 83, 94 (1964) and 17 g (1.05 equivalents) of pyridine in 600 ml of dichloromethane is ozonized (Wellsbach) at −78°. A precipitate (pyridine sulfur trioxide complex) is formed during the course of the reaction. Upon detecting ozone (color with aqueous KI solution) in the effluent stream, the ozone is stopped and the reaction mixture purged with nitrogen until all residual ozone is removed (no color with KI solution). The cold reaction mixture is poured into 3.5 L of pentane which is allowed to stir for one hour. The mixture is filtered and the filtrate evaporated in vacuo (bath temperature 25°) to yield 37 g of residue. This residue is taken up in ether and filtered from some insoluble material. The filtrate is evaporated in vacuo to yield 34.5 g (84%) of crude 1-ketopinic acid chloride as a slightly yellow solid foam. The crude product is treated with 0.25 equivalents (0.05 mol) of oxalyl chloride in benzene. The solvent and excess oxalyl chloride are removed to yield pure ketopinic acid chloride which crystallizes from pentane: $[\alpha]_D = -41°$ (C=1.9, $CHCl_3$).

EXAMPLE 2

1-Ketopinic Acid

A solution of 4.65 g (20 mmole) of 1-10-chloro-10-sulfinylidenecamphor and 1.60 g (20.3 mmole) of pyridine in 60 ml of dichloromethane is ozonized at −78° until ozone is detected in the effluent. The excess ozone is purged ($N_2$) and the cold reaction mixture poured into a stirring mixture of 80 ml of 1 N KOH and 100 ml of THF. The solution immediately turns black but lightens somewhat over 15 minutes. Stirring is continued for 45 minutes and the organic solvent removed under vacuum. The remaining basic (ca. pH 8) water layer is washed with ether (2×100 ml), covered with ether and acidified with 6 N $H_2SO_4$. The water layer is extracted with ether (3×100 ml) and the ether layer is washed with saturated NaCl, dried ($Na_2SO_4$) and evaporated to dryness to yield 3.0 g (83%) of 1-ketopinic acid: m.p. 225°–229° [Lit.[7] 232°–233°].

What is claimed is:

1. A method for preparing ketopinoyl acid halide, which comprises reacting 10-halo-10-sulfinylidenecamphor with ozone under basic conditions in the presence of an organic base, at reduced temperatures of within the range of from about $-40°$ C. to about $-100°$ C., to form the ketopinoyl halide, and recovering the ketopinoyl halide.

2. The method as defined in claim 1 wherein the starting 10-halo-10-sulfinylidenecamphor is employed in the form of a racemic mixture or as one of its antipodes.

3. The method as defined in claim 2 wherein the starting 10-halo-sulfinylidenecamphor is employed as its l-antipode.

4. The method as defined in claim 1 wherein the 10-halo-10-sulfinylidenecamphor is 10-chloro-10-sulfinylidenecamphor or 10-bromo-10-sulfinylidenecamphor.

5. The method as defined in claim 1 wherein the starting material is 1-10-chloro-10-sulfinylidenecamphor and the product is 1-ketopinoyl chloride.

6. The method as defined in claim 1 wherein the 10-halo-10-sulfinylidenecamphor is reacted with the ozone in the presence of an organic base and a chlorinated hydrocarbon solvent.

7. The method as defined in claim 6 wherein the organic base is pyridine, methylated pyridine, dimethylated pyridine or triethylamine and the chlorinated hydrocarbon solvent is dichloromethane or dichloroethane.

8. The method as defined in claim 1 wherein the reaction is carried out at a temperature of from about $-60°$ C. to about $-90°$ C.

9. A method for preparing ketopinic acid which comprises subjecting the ketopinoyl halide prepared as described in claim 1 to basic hydrolysis by treating the ketopinoyl halide with an alkali metal hydroxide or an alkaline earth metal hydroxide.

10. The method as defined in claim 9 wherein the ketopinoylhalide is 1-ketopinoyl chloride and the final product is 1-ketopinic acid.

* * * * *